(12) United States Patent
Kapadia (10) Patent No.: US 12,257,010 B2
(45) Date of Patent: Mar. 25, 2025

(54) SURGICAL ROBOTIC SYSTEMS (71) Applicant: Covidien LP, Mansfield, MA (US)

(72) Inventor: Jaimeen Kapadia, Cambridge, MA (US)

(73) Assignee: Covidien LP, Mansfield, MA (US)

( * ) Notice: Subject to any disclaimer, the term of this patent is extended or adjusted under 35 U.S.C. 154(b) by 941 days.

(21) Appl. No.: 17/291,059

(22) PCT Filed: Nov. 7, 2019

(86) PCT No.: PCT/US2019/060210
§ 371 (c)(1),
(2) Date: May 4, 2021

(87) PCT Pub. No.: WO2020/097293
PCT Pub. Date: May 14, 2020

(65) Prior Publication Data
US 2021/0386490 A1    Dec. 16, 2021

Related U.S. Application Data (60) Provisional application No. 62/756,731, filed on Nov. 7, 2018.

(51) Int. Cl.
*A61B 34/30* (2016.01)
*A61B 50/28* (2016.01)
(Continued)

(52) U.S. Cl.
CPC .............. *A61B 34/30* (2016.02); *A61B 50/28* (2016.02); *B25J 5/02* (2013.01); *B25J 9/0018* (2013.01); *B25J 9/0084* (2013.01)

(58) Field of Classification Search
None
See application file for complete search history.

(56) References Cited

U.S. PATENT DOCUMENTS 4,177,002 A * 12/1979 Motoda ...................... B25J 9/00
414/733
6,722,842 B1    4/2004 Sawdon et al.
(Continued)

FOREIGN PATENT DOCUMENTS

CA    2272040 A1 * 11/2000 ........... F16M 11/126
CN    108186120 A    6/2018
(Continued)

OTHER PUBLICATIONS

International Search Report dated Apr. 9, 2020, issued in corresponding international application No. PCT/US2019/060210, 3 pages.

*Primary Examiner* — Carl H Layno
*Assistant Examiner* — Manolis Pahakis
(74) *Attorney, Agent, or Firm* — Carter, DeLuca & Farrell LLP (57) ABSTRACT A surgical robotic system includes a ceiling mount assembly including a bracket configured to be fixed to a ceiling, and an elongate body extending horizontally from the bracket and defining a longitudinally-extending track. The surgical robotic system further includes a plurality of robotic arms coupled to a ceiling of an operating room via the ceiling mount assembly, wherein the plurality of robotic arms is configured to move along a horizontal axis defined by the track.

18 Claims, 4 Drawing Sheets

(51) Int. Cl.
*B25J 5/02* (2006.01)
*B25J 9/00* (2006.01)

(56) References Cited

U.S. PATENT DOCUMENTS

| | | | | |
|---|---|---|---|---|
| 6,788,018 | B1* | 9/2004 | Blumenkranz | B25J 9/1065 318/568.25 |
| 8,267,884 | B1* | 9/2012 | Hicks | A61B 18/042 604/23 |
| 2009/0003975 | A1* | 1/2009 | Kuduvalli | B25J 9/0084 901/19 |
| 2009/0147924 | A1* | 6/2009 | Gross | A61B 6/56 378/194 |
| 2009/0247993 | A1* | 10/2009 | Kirschenman | A61B 34/71 606/1 |
| 2010/0256558 | A1* | 10/2010 | Olson | A61B 34/77 604/95.01 |
| 2011/0274247 | A1* | 11/2011 | Maschke | A61B 6/4441 378/62 |
| 2011/0280379 | A1* | 11/2011 | Maschke | A61B 6/4458 901/15 |
| 2017/0181720 | A1* | 6/2017 | Akiyama | A61B 6/56 |
| 2018/0214100 | A1* | 8/2018 | Kumar | A61B 6/4429 |
| 2018/0256270 | A1* | 9/2018 | Cooper | A61B 34/71 |
| 2020/0315738 | A1* | 10/2020 | Dewaele | A61B 34/71 |

FOREIGN PATENT DOCUMENTS

| | | | | |
|---|---|---|---|---|
| WO | WO-2004028754 A1 * | 4/2004 | | B25J 5/007 |
| WO | 2010044536 A1 | 4/2010 | | |
| WO | 2018181040 A1 | 10/2018 | | |

* cited by examiner

SURGICAL ROBOTIC SYSTEMS

CROSS REFERENCE TO RELATED APPLICATIONS

The present application is a national stage application of International Patent Application No. PCT/US2019/060210, filed on Nov. 7, 2019, which claims the benefit of and priority to U.S. Provisional Application No. 62/756,731, filed on Nov. 7, 2018. Each of the foregoing applications is hereby incorporated by reference in its entirety.

BACKGROUND

Surgical robotic systems have been used in minimally invasive medical procedures. Some surgical robotic systems included a console or cart supporting a surgical robotic arm and a surgical instrument having at least one end effector (e.g., forceps or a grasping tool) mounted to the robotic arm. The robotic arm provided mechanical power to the surgical instrument for its operation and movement.

Manually-operated surgical instruments often included a handle assembly for actuating the functions of the surgical instrument. However, when using a robotic surgical system, no handle assembly was typically present to actuate the functions of the end effector. Accordingly, to use each unique surgical instrument with a robotic surgical system, an instrument drive unit was used to interface with the selected surgical instrument to drive operations of the surgical instrument.

SUMMARY

In accordance with an aspect of the present disclosure, a surgical robotic system is provided and includes a ceiling mount assembly and a plurality of robotic arms. The ceiling mount assembly includes a bracket configured to be fixed to a ceiling, and an elongate body extending horizontally from the bracket and defining a longitudinally-extending track. The robotic arms are coupled to the track of the elongate body and are configured to move along a horizontal axis defined by the track.

In aspects, the ceiling mount assembly may further include a trolley assembly slidably coupled to the track of the elongate body. The robotic arms may extend distally from the trolley assembly.

In further aspects, the trolley assembly may include a proximal segment slidably received in the track of the elongate body, and a distal segment rotatably coupled to the proximal segment. A proximal end portion of each of the robotic arms may be non-rotatably coupled to the distal segment of the trolley assembly, such that the robotic arms are rotatable about a vertical axis defined by the trolley assembly.

In other aspects, the robotic arms may have a telescopic proximal end portion configured to move between a retracted configuration, in which the robotic arms have a first height, and an extended configuration, in which the robotic arms have a second height, taller than the first height.

In aspects, each of the robotic arms may have a proximal end portion coupled to the track of the elongate body. The proximal end portions of the robotic arms may be parallel and in side-by-side relation with one another.

In further aspects, each of the robotic arms may have a distal end portion pivotably coupled to a respective proximal end portion thereof.

In other aspects, the surgical robotic system may further include a plurality of elongated slides attached to a respective distal end portion of the robotic arms. Each of the slides may be configured to slidably secure a surgical instrument thereto.

In some aspects, the surgical robotic system may further include a plurality of instrument drive units slidably coupled to a respective slide. Each of the instrument drive units may be configured to drive various operations of a respective surgical instrument.

In aspects, each of the slides may be rotatable relative to a respective distal end portion of the robotic arms.

In further aspects, the elongate body may have a first end portion rotationally coupled to the bracket such that swiveling of the elongate body relative to the bracket adjusts a circumferential position of the robotic arms about the bracket.

In another aspect of the present disclosure, a surgical robotic system is provided and includes a ceiling mount assembly and a cluster of robotic arms. The ceiling mount assembly includes a bracket configured to be fixed to a ceiling, and a hub rotationally coupled to the bracket. The robotic arms are disposed in side-by-side relation to one another and coupled to the hub. The robotic arms are configured to rotate with the hub relative to the bracket.

In some aspects, the ceiling mount assembly may further include an elongate body coupled to the bracket and defining a longitudinally-extending track. The robotic arms may be coupled to the track of the elongate body, such that the robotic arms are movable along a horizontal axis defined by the track.

In other aspects, the hub may be a trolley assembly slidably coupled to the track of the elongate body.

In yet another aspect of the present disclosure, a surgical robotic system is provided and includes a ceiling mount assembly and a cluster of robotic arms. The ceiling mount assembly includes a bracket configured to be fixed to a ceiling, an elongate body, and a hub. The elongate body extends horizontally from the bracket and defines a longitudinally-extending track. The elongate body has a first end portion rotationally coupled to the bracket. The hub is coupled to the track of the elongate body and configured to both slide along a horizontal axis defined by the track and rotate relative to the bracket about a vertical axis defined by the hub. The robotic arms are disposed in side-by-side relation to one another and coupled to the hub. The robotic arms are configured to rotate with the hub about the vertical axis, slide with the hub along the horizontal axis, and move along a circumferential path about the bracket during swiveling of the elongate body.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Embodiments of the presently disclosed surgical robotic system and ceiling mount assemblies thereof are described in detail with reference to the drawings, in which like reference numerals designate identical or corresponding elements in each of the several views. As used herein, the term "distal" refers to that portion of the surgical robotic system or component thereof that is closest to the patient, while the term "proximal" refers to that portion of the surgical robotic system or component thereof further from the patient.

As will be described in detail below, provided is a ceiling mount assembly for mounting surgical robotic arms to a ceiling or other fixture in an operating room. The ceiling mount assembly has a bracket affixable to a ceiling, a swivel arm rotationally coupled to and extending from the bracket, and a trolley assembly slidably and rotationally coupled to the swivel arm. A cluster of robotic arms may be attached to the trolley assembly, such that as the trolley assembly rotates about a vertical axis, so does the cluster of robotic arms, and as the trolley assembly traverses a horizontal axis defined by the swivel arm, so does the cluster of robotic arms. Moreover, as the swivel arm swivels relative to the bracket, the cluster of robotic arms moves along a circumferential path about the bracket. In some aspects, the robotic arms may each have a telescopic portion that couples the robotic arms to the trolley assembly, allowing the vertical height of the arms to be adjusted. Other features and benefits of the disclosed ceiling mount assemblies are further detailed below.

Figure 1:
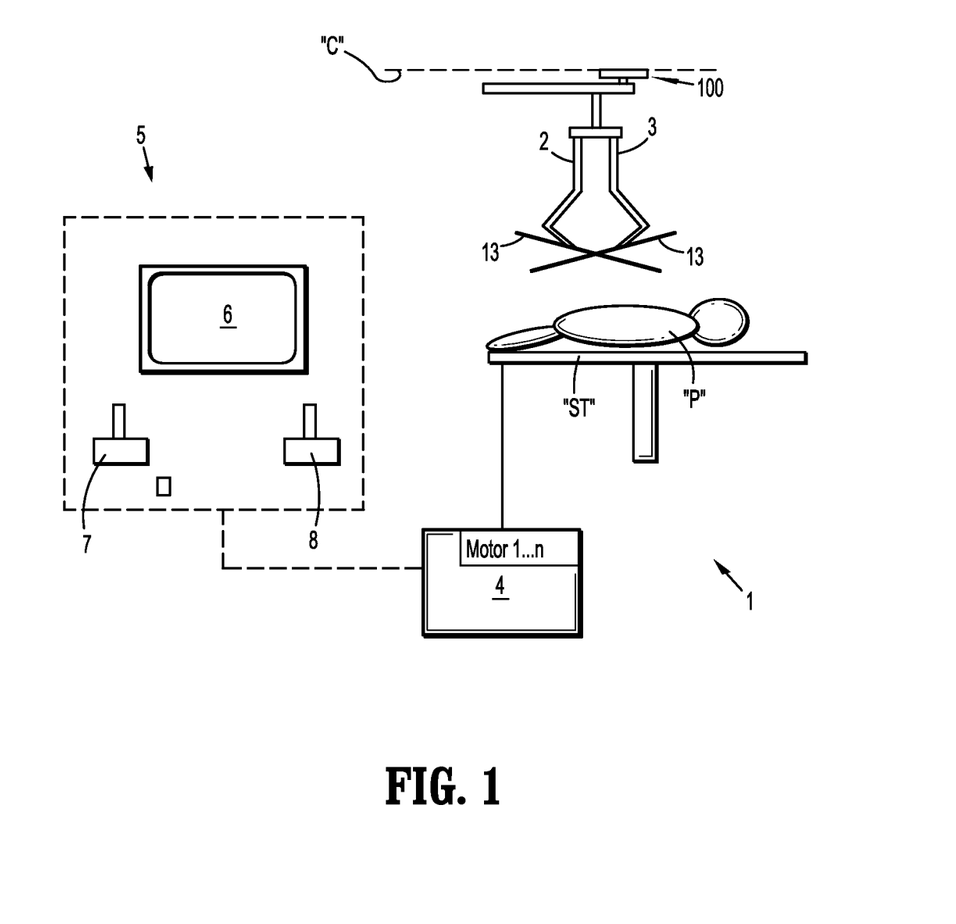
FIG. 1 is a schematic illustration of a surgical robotic system including a ceiling mount assembly for mounting a plurality of robotic arms to a ceiling of an operating room in accordance with the present disclosure.
Figure 2:
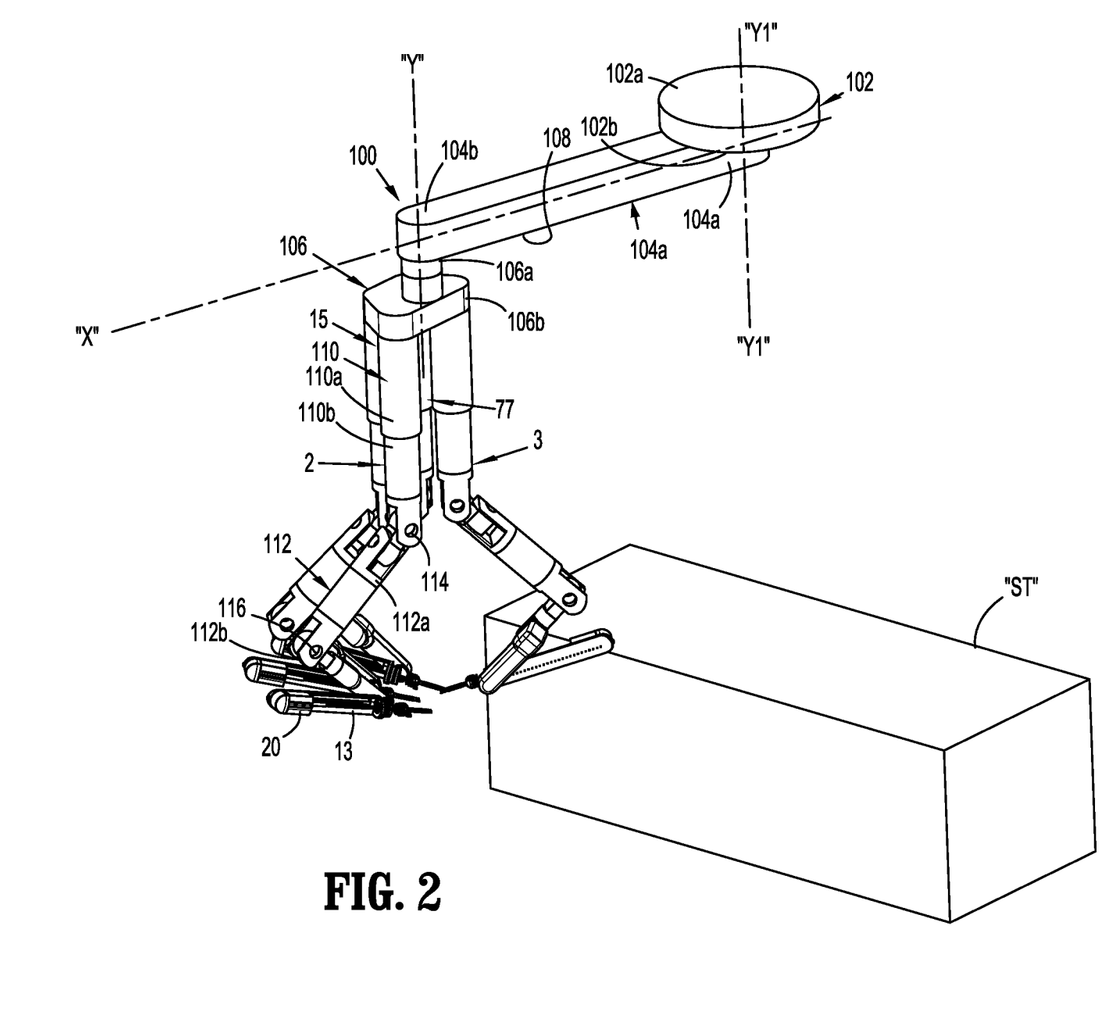
FIG. 2 is a perspective view of the ceiling mount assembly and robotic arms of FIG. 1, with the ceiling mount assembly and robotic arms in a first spatial orientation relative to a surgical table.

Referring initially to FIGS. 1 and 2, a surgical system, such as, for example, a surgical robotic system 1, generally includes a plurality of surgical robotic arms 2, 3, 15, 17 mounted to a ceiling "C" of an operating room via a ceiling mount assembly 100; an elongated slide 13 coupled to an end of each of the robotic arms 2, 3, 15, 17; an instrument drive unit 20 removably attached to the slide 13 and configured to move along the slide 13; a control device 4; and an operating console 5 coupled with control device 4. The surgical robotic system 1 is configured for use on a patient "P" lying on a surgical table "ST" to be treated in a minimally invasive manner by means of a surgical instrument, e.g., an electromechanical instrument (not shown).

The robotic arms 2, 3 may be driven by electric drives (not shown) that are connected to the control device 4. In other embodiments, the robotic arms 2, 3, may include a pneumatic drive system driven by, for example, central air in an operating room. The control device 4 (e.g., a computer) is set up to activate the drives, in particular by means of a computer program, in such a way that the robotic arms 2, 3, 15, 17, the attached instrument drive units 20, and an electromechanical instrument (not shown) execute a desired movement according to a movement defined by means of manual input devices 7, 8 of the operating console 5. The control device 4 may also be set up in such a way that it regulates the movement of the instrument drive unit 20 along the slide 13, movement of the robotic arms 2, 3, 15, 17, and/or movement of the drives.

For a detailed discussion and illustration of exemplary robotic arms 2, 3, 15 and 17, slides 13, and instrument drive units 20, reference may be made to U.S. patent application Ser. No. 15/737,838, filed on Dec. 19, 2017, the entire content of which is incorporated herein by reference.

The control device 4 may control a plurality of motors, e.g., motors (Motor 1 . . . n), with each motor configured to drive movement of the robotic arms 2, 3, 15, 17 in a plurality of directions. Further, the control device 4 may control a plurality of drive motors (not shown) of the ceiling mount assembly 100 to drive various movements of components of the ceiling mount assembly 100, as will be described. Further still, the control device 4 may control a plurality of drive motors (not shown) of the instrument drive unit 20 to drive various operations of the attached surgical instrument. The instrument drive unit 20 transfers power and actuation forces from its motors to driven members (not shown) of the electromechanical instrument to ultimately drive movement of components of an end effector of the electromechanical instrument, for example, a movement of a knife blade (not shown) and/or a closing and opening of jaw members of the end effector.

The operating console 5 includes a display device 6 and the manual input devices 7, 8. The display device 6 is set up in particular to display three-dimensional images, and the manual input devices 7, 8 are utilized by a person (not shown), for example a surgeon, to telemanipulate robotic arms 2, 3, 15, 17 in a first operating mode, as known in principle to a person skilled in the art.

For a detailed description of the construction and operation of a robotic surgical system, reference may be made to U.S. Pat. No. 8,828,023, entitled "Medical Workstation," the entire contents of which are incorporated by reference herein.

Figure 3:
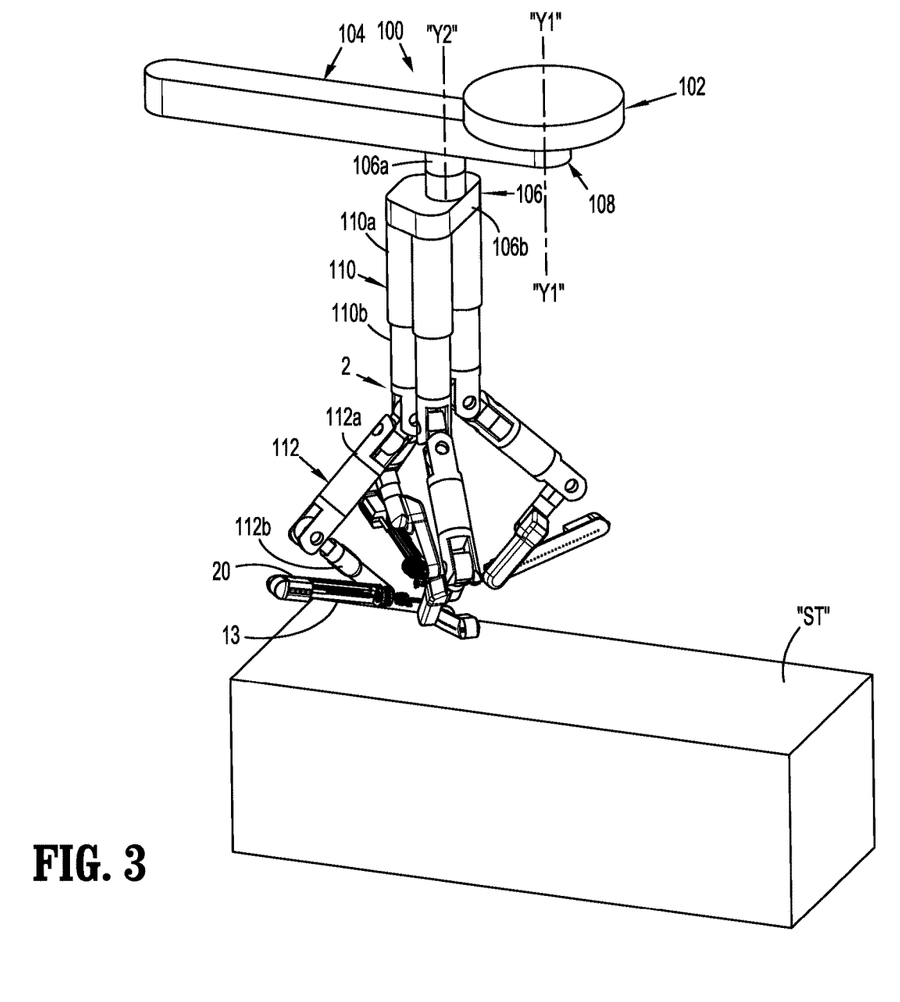
FIG. 3 is a perspective view of the ceiling mount assembly and robotic arms of FIG. 1, with the ceiling mount assembly and robotic arms in a second spatial orientation relative to the surgical table.

With reference to FIGS. 2 and 3, the ceiling mount assembly 100 and the surgical robotic arms 2, 3, 15, and 17 will now be described in detail. The ceiling mount assembly 100 generally includes a bracket or mount 102 configured to be secured to a fixture in an operating room (e.g., a ceiling), an elongate body 104 rotationally coupled to the bracket 102, and a hub 106 slidably coupled to the elongate body 104. The surgical robotic arms 2, 3, 15, and 17 are coupled to the hub 106 in a clustered configuration. In aspects, the surgical robotic system 1 may include more than one ceiling mount assemblies 100 for coupling a corresponding cluster of robotic arms.

The bracket 102 of the ceiling mount assembly 100 may be a plate configured to be fastened to a ceiling of the operating room via any suitable fastening engagement. For example, the bracket 102 may be fastened to a ceiling via welding, screws, nails, adhesives, rivets, studs, bolts, magnets, suction cups, or the like. In embodiments, the bracket 102 may assume any suitable shape, such as, for example, dome-shaped, polygonal, or the like. The bracket 102 has an upper surface 102a that may be flush with the ceiling "C" or recessed in the ceiling "C", and a lower surface 102b. It is contemplated that the bracket 102 may be hung from other suitable fixed surfaces in an operating room.

The elongate body 104 of the ceiling mount assembly 100 may be configured as a swivel arm extending radially outward from a center of the bracket 102. The elongate body 104 has a first end portion 104a rotationally coupled to the lower surface 102b of the bracket 102, about a rotation axis "Y1", and a second end portion 104b. The elongate body 104 has a track 108 defined along its length between the first and second end portions 104a, 104b thereof. The track 108 defines a horizontal axis "X" along which the hub 106 of the ceiling mount assembly 100 may be configured to slide. The track 108 may be a box track, a round track, or any track suitable to support the hub 106 while also permitting the hub 106 to slide therealong. The elongate body 104 may have a telescopic configuration to allow for automated or manual adjustment of the length of the elongate body 104.

In embodiments, the elongate body 104 may be pivotable in relation to the bracket 102 between a first orientation, in which the elongate body 104 is parallel with the bracket 102, and thus the ceiling "C," and a plurality of second orientations, in which the elongate body 104 extends at a non-zero angle from the bracket 102, and thus the ceiling "C."

The hub 106 of the ceiling mount assembly 100 may be configured as a trolley assembly that rolls along the horizontal axis "X" of the track 108 of the elongate body 104. The hub 106 includes a proximal segment 106a slidably received and supported in the track 108 of the elongate body 104, and a distal segment 106b rotationally coupled to the proximal segment 106a. The proximal segment 106a may be a wheeled bracket hung from the track 108 of the elongate body 104 to allow the hub 106 to slide along the track 108 by rolling. The distal segment 106b may be a load bar that is rotatable relative to the proximal segment 106a about a vertical axis "Y2" defined by the hub 106. The vertical axis "Y2" defined by the hub 106 is perpendicular to the horizontal axis "X" defined by the track 108 of the elongate body 104, and may be parallel to rotation axis "Y1." In embodiments, the hub 106 may be disposed at other suitable angles relative to the track 108.

With continued reference to FIGS. 2 and 3, the robotic arms 2, 3, 15, 17 are clustered with one another and disposed in side-by-side relation. Each of the robotic arms 2, 3, 15, 17 has a proximal end portion 110 supported on the load bar 106b of the hub 106, and a distal end portion 112 pivotably coupled to the proximal end portion 110. The proximal end portion 110 of each of the robotic arms 2, 3, 15, 17 may be parallel with one another. The proximal end portion 110 of each of the robotic arms 2, 3, 15, 17 are coupled to the load bar 106b of the hub 106, such that rotation of the load bar 106b of the hub 106 about the vertical axis "Y2" relative to the wheeled bracket 106a of the hub 106 causes the robotic arms 2, 3, 15, 17 to rotate as one unit about the vertical axis "Y2." Further, since the robotic arms 2, 3, 15, 17 are connected to the hub 106, the robotic arms 2, 3, 15, 17 move along the horizontal axis "X" of the track 108 as the hub 106 traverses the track 108. Further still, swiveling of the elongate body 104 about the bracket 102 adjusts a circumferential position of the robotic arms 2, 3, 15, 17 about the bracket 102. In embodiments, each of the robotic arms 2, 3, 15, 17 may be independently rotatable relative to the load bar 106b of the hub 106.

Due to the robotic arms 2, 3, 15, 17 having substantially similar features, or in some aspects, identical features, only the features of robotic arm 2 will be described in detail. The proximal end portion 110 of the robotic arm 2 may have a telescopic configuration to permit an adjustment of the vertical height of the proximal end portion 110. For example, the proximal end portion 110 of the robotic arm 2 may be constructed from a pair of concentric tubular members 110a, 110b, where one of the tubular members, for example, tubular member 110b, is slidable within and relative to the other of the tubular members, for example, tubular member 110a. As such, the proximal end portion 110 of the robotic arm 2 may be transitionable between a retracted configuration, in which robotic arm 2 has a first height, and an extended configuration, in which the robotic arm 2 has a second height, taller than the first height. It is contemplated that the heights of the robotic arms 2, 3 are independently adjustable. In some aspects, the proximal end portion 110 of the robotic arms 2, 3, may be gravity compensated to allow for manual height adjustment thereof.

The distal end portion 112 of the robotic arm 2 is pivotably coupled to the proximal end portion 110 thereof via a joint 114. The distal end portion 112 of the robotic arm 2 may be constructed from a pair of proximal and distal shaft members 112a, 112b pivotably coupled to one another via a joint 116. The distal shaft member 112b of each of the robotic arms 2, 3, 15, 17 has a respective slide 13 rotatably coupled thereto.

As can be appreciated, the ceiling mount assembly 100 includes a plurality of drive motors (not shown), such as, for example, electric motors, arranged throughout, which are responsible for driving each discrete movement of the components of the ceiling mount assembly 100. For example, a first motor (not shown) of the ceiling mount assembly 100 is operably coupled to the first end portion 104a of the elongate body 104 to drive the swiveling motion of the elongate body 104 relative to the bracket 102; a second motor (not shown) of the ceiling mount assembly 100 is operably coupled to the wheel bracket 106a of the hub 106 to drive the sliding movement of the hub 106 along the track 108 of the elongate body 104; and a third motor (not shown) of the ceiling mount assembly 100 is operably coupled to the load bar 106b of the hub 106 to drive the rotation of the load bar 106b about the vertical axis "Y2."

It is contemplated that the drive motors of the ceiling mount assembly 100 may be driven via any suitable drive mechanism, such as, for example, a gear assembly, a rack and pinion, pulley friction drive, hydraulics, pneumatics, a cable, belt, or the like. The control device 4 may be in wireless or electrical communication with the drive motors of the ceiling mount assembly 100 to bestow a clinician or computer software with the ability to control the operation of each of the drive motors. It is contemplated that components of the ceiling mount assembly 100 may use constant force springs or suspended weights for gravity compensation.

In operation, a position of one or more components of the surgical robotic system 1 may be adjusted relative to a patient "P" lying on a surgical table "ST." For example, to adjust the angular orientation of the robotic arms 2, 3, 15, 17, the load bar 106b of the hub 106 may be activated via the control device 4 to rotate about the vertical axis "Y2" of the hub 106 relative to the wheeled bracket 106a of the hub 106. Since each of the robotic arms 2, 3, 15, 17 is attached to the load bar 106b, rotation of the load bar 106b changes the angular orientation of the robotic arms 2, 3, 15, 17 from a first angular orientation, as shown in FIG. 2, to a second angular orientation, as shown in FIG. 3.

To adjust a position of the robotic arms 2, 3, 15, 17 along a horizontal plane parallel with the patient "P," the wheeled bracket 106a of the hub 106 may be activated by the control device 4 to move along the horizontal axis "X" defined by the track 108 of the elongate body 104. Given that the robotic arms 2, 3, 15, 17 are attached to the hub 106, the position of the robotic arms 2, 3, 15, 17 along the horizontal plane is adjusted as the hub 106 moves from a first position, as shown in FIG. 2, to a second position, as shown in FIG. 3.

To adjust a circumferential position of the robotic arms 2, 3, 15, 17 about the bracket 102, the first end portion 104a of the elongate body 104 may be activated by the control device 4 to rotate about the bracket 102. Since the robotic arms 2, 3, 15, 17 are attached to the hub 106, and the hub 106 is attached to the elongate body 104, the swiveling motion of the elongate body 104 about the bracket 102 moves the robotic arms 2, 3, 15, 17 along a circumferential pathway about the bracket 102.

Figure 4:
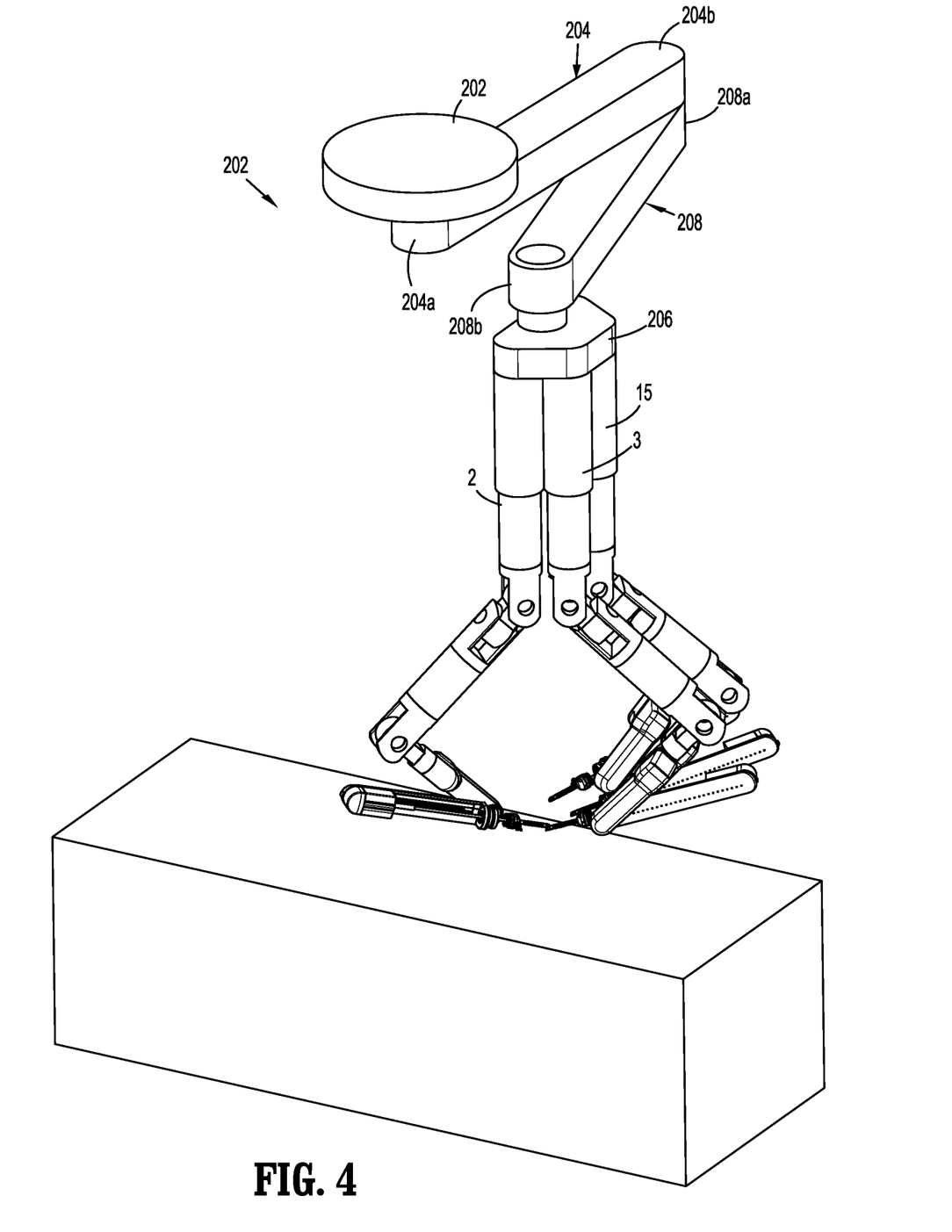
FIG. 4 is a perspective view of another embodiment of a ceiling mount assembly having the robotic arms of FIG. 1 attached thereto.

With reference to FIG. 4, another embodiment of a ceiling mount assembly 200 is illustrated, similar to the ceiling mount assembly 100 described above. Due to the similarities between the ceiling mount assembly 200 of the present embodiment and the ceiling mount assembly 100 described above, only those elements of the ceiling mount assembly 200 deemed necessary to elucidate the differences from ceiling mount assembly 100 described above will be described in detail.

The ceiling mount assembly 200 generally includes a bracket or mount 202 configured to be secured to a fixture in an operating room (e.g., a ceiling), a pair of first and second elongate bodies 204, 208, and a hub 206. The surgical robotic arms 2, 3, 15 are coupled to the hub 206 in a clustered configuration. The first elongate body 204 has a first end 204a rotationally coupled to the mount 202, and a second end 204b. The second elongate body 208 has a first end 208a rotationally coupled to the second end 204b of the first elongate body 204. In embodiments, more than two elongate bodies may be provided. The hub 206 is coupled to the second elongate body 208 and may be slidable relative thereto along a longitudinal axis defined by the second elongate body 208. In other embodiments, the hub 206 may be axially fixed to a second end 208b of the second elongate body 208 or any suitable location along the second elongate body 208. The components of the ceiling mount assembly 200 may be gravity compensated to allow for a manual adjustment of their relative positions while self-maintaining their selected relative positions. As illustrated, the mount 202, the first elongate body 204, the second elongate body 208, and the hub 206, lie on different horizontal planes. In other embodiments, one or more of the components of the ceiling mount assembly 200 may be coplanar. It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. A surgical robotic system, comprising:
    a ceiling mount assembly including:
        a bracket configured to be fixed to a ceiling; and
        an elongate body extending horizontally from the bracket and defining a longitudinally-extending track, wherein the elongate body has a first end portion rotationally coupled to the bracket; and
    a plurality of robotic arms coupled to the track of the elongate body, wherein the plurality of robotic arms is configured to move along a horizontal axis defined by the track, wherein swiveling of the elongate body relative to the bracket adjusts a circumferential position of the plurality of robotic arms about the bracket.

2. The surgical robotic system according to claim 1, wherein the ceiling mount assembly further includes a trolley assembly slidably coupled to the track of the elongate body, the plurality of robotic arms extending distally from the trolley assembly.

3. The surgical robotic system according to claim 2, wherein the trolley assembly includes:
    a proximal segment slidably received in the track of the elongate body; and
    a distal segment rotatably coupled to the proximal segment, a proximal end portion of each of the plurality of robotic arms being non-rotatably coupled to the distal segment of the trolley assembly, such that the plurality of robotic arms are rotatable about a vertical axis defined by the trolley assembly.

4. The surgical robotic system according to claim 1, wherein at least one robotic arm of the plurality of robotic arms has a telescopic proximal end portion configured to move between a retracted configuration, in which the at least one robotic arm has a first height, and an extended configuration, in which the at least one robotic arm has a second height, taller than the first height.

5. The surgical robotic system according to claim 1, wherein each of the plurality of robotic arms has a proximal end portion coupled to the track of the elongate body, the proximal end portion of each of the plurality of robotic arms being parallel and in side-by-side relation with one another.

6. The surgical robotic system according to claim 5, wherein each of the plurality of robotic arms has a distal end portion pivotably coupled to a respective proximal end portion.

7. The surgical robotic system according to claim 6, further comprising a plurality of elongated slides attached to a respective distal end portion of the plurality of robotic arms, wherein each of the plurality of slides is configured to slidably secure a surgical instrument thereto.

8. The surgical robotic system according to claim 7, further comprising a plurality of instrument drive units slidably coupled to a respective slide, wherein each of the plurality of instrument drive units is configured to drive various operations of a respective surgical instrument.

9. The surgical robotic system according to claim 7, wherein each of the plurality of slides is rotatable relative to a respective distal end portion of the plurality of robotic arms.

10. A surgical robotic system, comprising:
    a ceiling mount assembly including:
        a bracket fixed to a ceiling; and
        an elongate body extending horizontally from the bracket and defining a longitudinally-extending track, wherein the elongate body has a first end portion rotationally coupled to the bracket; and
    a pair of robotic arms coupled to the track of the elongate body, wherein each robotic arm is configured to move along a horizontal axis defined by the track, wherein rotating the elongate body relative to the bracket adjusts a circumferential position of the pair of robotic arms about the bracket.

11. The surgical robotic system according to claim 10, wherein the elongate body defines a longitudinally-extending track, and wherein the ceiling mount assembly further includes a trolley assembly slidably coupled to the track of the elongate body, each robotic arm extending distally from the trolley assembly.

12. The surgical robotic system according to claim 11, wherein the trolley assembly includes:
    a proximal segment slidably received in the track of the elongate body; and a distal segment rotatably coupled to the proximal segment, a proximal end portion of each robotic arm being non-rotatably coupled to the distal segment of the trolley assembly, such that each robotic arm is rotatable about a vertical axis defined by the trolley assembly.

13. The surgical robotic system according to claim 10, wherein each robotic arm has a telescopic proximal end portion configured to move between a retracted configuration, in which each robotic arm has a first height, and an extended configuration, in which each robotic arm has a second height, taller than the first height.

14. The surgical robotic system according to claim 10, wherein the pair of robotic arms includes a plurality of robotic arms, wherein each robotic arm of the plurality of robotic arms has a proximal end portion coupled to the track of the elongate body, the proximal end portion of each robotic arm of the plurality of robotic arms being parallel and in side-by-side relation with one another.

15. The surgical robotic system according to claim 14, wherein each robotic arm of the plurality of robotic arms has a distal end portion pivotably coupled to a respective proximal end portion.

16. The surgical robotic system according to claim 15, further comprising a plurality of elongated slides, wherein each elongated slide of the plurality of elongated slides is attached to a respective distal end portion of a robotic arm of the plurality of robotic arms, wherein each elongated slide of the plurality of elongated slides is configured to slidably secure a surgical instrument thereto.

17. The surgical robotic system according to claim 16, further comprising a plurality of instrument drive units slidably coupled to a respective elongated slide, wherein each instrument drive unit of the plurality of instrument drive units is configured to drive various operations of a respective surgical instrument.

18. The surgical robotic system according to claim 16, wherein each elongated slide of the plurality of elongated slides is rotatable relative to a respective distal end portion of a robotic arm of the plurality of robotic arms.

\* \* \* \* \*